United States Patent [19]

Hofmeier et al.

[11] Patent Number: 4,714,527
[45] Date of Patent: Dec. 22, 1987

[54] PROCESS FOR MEASURING THE POTENTIAL DIFFERENCE BETWEEN A SAMPLE LIQUID AND A REFERENCE ELECTROLYTE

[75] Inventors: Gerhard Hofmeier; Karl Petersen; Wolfgang Schroeder, all of Hamburg, Fed. Rep. of Germany

[73] Assignee: Eppendorf Geratebau Netheler + Hinz GmbH, Hamburg, Del.X

[21] Appl. No.: 860,860

[22] Filed: May 8, 1986

[30] Foreign Application Priority Data

May 11, 1985 [DE] Fed. Rep. of Germany ....... 3517131

[51] Int. Cl.[4] ........................................... G01N 27/46
[52] U.S. Cl. ..................................... 204/1 T; 204/416; 204/435
[58] Field of Search ................. 204/1 T, 435, 416–420

[56] References Cited

U.S. PATENT DOCUMENTS

| | | | |
|---|---|---|---|
| 3,658,679 | 4/1972 | Stansell et al. | 204/435 |
| 4,490,234 | 12/1984 | Buzza | 204/415 |
| 4,544,455 | 10/1985 | Eisenhardt et al. | 204/435 |
| 4,592,823 | 6/1986 | Gregory | 204/402 |

FOREIGN PATENT DOCUMENTS 83109541.9  9/1983  European Pat. Off. .

Primary Examiner—T. Tung
Attorney, Agent, or Firm—Lane & Aitken

[57] ABSTRACT

In a process for measuring the potential difference between a flow of sample liquid delivered by pumping and a reference electrolyte in which the sample flow is brought into contact with a reference electrode, the reference electrode contains a capillary channel, which extends substantially at right angles to the sample flow. The reference electrolyte is pumped at right angles to the capillary channel over its open end and the pumping of the flow of sample liquid and the flow of reference electrolyte starts and finishes simultaneously.

4 Claims, 3 Drawing Figures

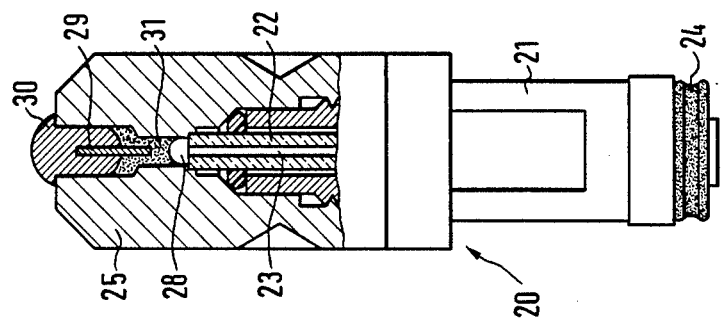
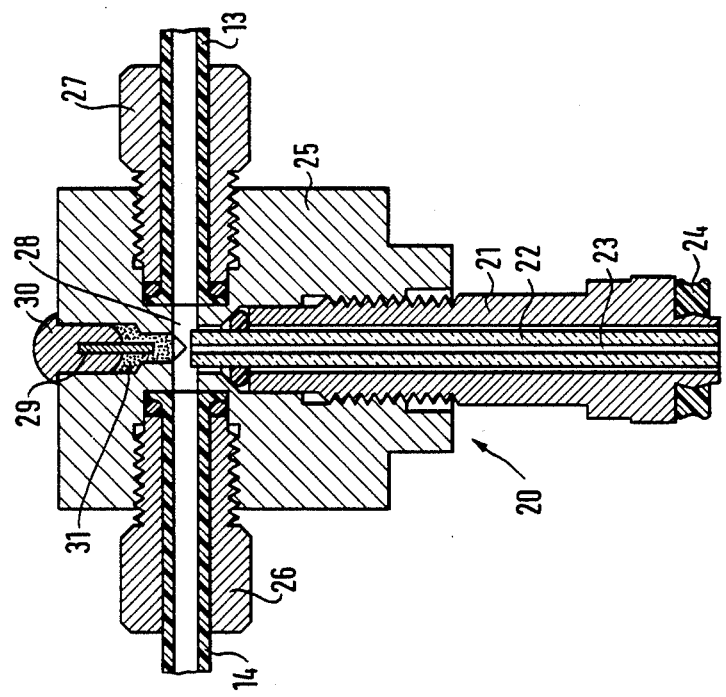

PROCESS FOR MEASURING THE POTENTIAL DIFFERENCE BETWEEN A SAMPLE LIQUID AND A REFERENCE ELECTROLYTE

BACKGROUND OF THE INVENTION

1. Field of the Invention

The present invention relates to a process for measuring the potential difference between a sample liquid flow delivered by pumping and a reference electrolyte, in which the sample flow is brought into contact with a reference electrode having a capillary channel extending substantially at right angles or transversely to the sample flow, one end of said capillary channel opening into said flow, wherein reference electrolyte, coupled to a reference element of the reference electrode, is fed into the other end of said capillary channel.

The invention also relates to an apparatus for measuring the ionic concentration in a sample liquid, as well as a reference electrode for performing the process and/or for the apparatus.

2. Description of the Related Art

In a known process for measuring the ionic concentration in a sample liquid (European Patent Applicaton Serial No. 0 105 434), the reference electrolyte is located in a tank above the channel, through which the sample liquid is pumped, and the interior of the tank is connected to a channel for the sample liquid via a capillary channel through which, under the influence of gravity, reference electrolyte passes out of the tank and into the sample channel. By means of a reference element immersed in the electrolytic tank, the potential difference between the sample liquid and the reference electrolyte is measured, in order to obtain a reference value for the potentials characterizing the ionic concentrations measured by means of the ion selective electrode or electrodes.

The known process suffers from the disadvantage that reference electrolyte passes permanently, i.e., also when no ionic concentration measurement is taking place, from the electrolytic tank into the sample channel via the capillary channel. This leads to a considerable reference electrolyte loss, unless the capillary channel has an extremely small cross-section. However, a small cross-section greatly increases the risk of the capillary channel becoming clogged. Then the electrolytic tank has to be emptied in the known arrangement for replacing the capillary body having the capillary channel. Finally, in the known system it is only possible to select a construction in which the electrolytic tank is positioned above the sample channel, because only then can the reference electrolyte pass by gravity into the sample channel.

In connection with a process for measuring the potential difference between a sample liquid and a reference electrolyte, the object of the invention is to reduce the reference electrolyte consumption, reduce the risk of clogging the electrolyte channel, and continuously remove from the reference electrolyte constituents gassing out, inter alia, in the vicinity of the reference element.

SUMMARY OF THE INVENTION

According to the invention this problem is solved by a process of the aforementioned type in that a flow of reference electrolyte is pumped transversely or pumped at right angles to the capillary channel over its other end and that the pumping of the reference electrolyte flow is started before measuring the potential difference.

In the process according to the invention, which is used, for example, in conjunction with the measurement of the ionic concentration in the sample liquid, but is used in an alternative embodiment as a calibration process, before the start of the measuring process and preferably throughout the measuring process, the reference electrolyte is conveyed through the capillary channel, so that constituents gassing therefrom are continuously removed and cannot falsify the measurement. As reference electrolyte only has to flow during the measuring process, the reference electrolyte consumption is significantly reduced.

There is also no need to dimension the capillary channel with a view to obtain a low reference electrolyte consumption, so that the clogging risk is reduced. Moreover, the electrolyte channel does not have to be positioned above the sample or measuring channel, because the conveying of reference electrolyte to the capillary channel takes place by pumping and not by gravity.

In order to achieve in a simple manner a preferred simultaneous starting and a preferred simultaneous finishing of the pumping of sample liquid and reference electrolyte, the sample liquid flow and reference electrolyte flow can be passed through hoses, which engage with the rotary piston of a hose pump and are juxtaposed in the axial direction of the rotary piston.

When measuring the ionic concentration in the sample liquid, sample liquid is conventionally conveyed to an ion selective electrode or several ion selective electrodes, so that for performing the measurement the sample liquid is then kept for a longer period in contact with the ion selective electrode or electrodes, without any further sample liquid delivery taking place. In order to ensure an adequate reference electrolyte supply to the capillary channel during this measuring time, the reference electrolyte flow can be pumped into a pressure reservoir, which follows the other end of the capillary channel and from which the reference electrolyte can only flow slowly, preferably via a restrictor. Thus, the reference electrolyte pressure over the other end of the capillary channel is maintained for a longer period of time, such as the measuring time.

The invention also relates to an apparatus for measuring the ionic concentration in a sample liquid with a flow channel for delivering sample liquid, in whose wall is provided at least one ion selective electrode, as well as one end of a capillary channel forming part of a reference electrode and whose other end is connected to a zone for receiving reference electrolyte which is coupled to the reference element of the reference electrode. According to the invention, this apparatus is characterized in that the zone for receiving the reference electrolyte is an electrolytic channel extending transversely or at right angles to the longitudinal extension of the capillary channel, whose other end is connected to a hose pump, to which is also connected the flow channel for the sample liquid and in that the other end of the electrolyte channel is connected to a pressure reservoir.

The pressure reservoir preferably comprises an elastically expandable hose, it being followed in one embodiment by a restrictor, such as a helically wound, inelastic hose, whose internal cross-section is much smaller, i.e., at the most half as large as the internal cross-section of the hose-like pressure reservoir.

For performing the inventive process and for use in the inventive apparatus it is possible to provide a reference electrode, which is characterized by a capillary body arranged in a capillary support and having a capillary channel, whereof one end extends into an electrolytic channel extending transversely or at right angles to the longitudinal axis of the capillary channel, as well as by a reference element provided opposite to one end of the capillary channel and on the electrolytic channel side remote therefrom which reference element can be electrically connected to an evaluation circuit.

As a result of the T-shaped arrangement of the capillary channel and the electrolytic channel, as well as through the pumping of reference electrolyte through the electrolytic channel, it is ensured that no air bubbles can be deposited in the electrolytic channel in the vicinity of one end of the capillary channel which could interrupt the supply of reference electrolyte to the capillary channel and therefore interrupt the electrical connection between sample or measuring channel and reference element. In the vicinity of the reference element constituents which may be gassed out of the reference electrolyte and which could lead to erroneous reference potential measurements are continuously removed.

It has been found that, when using a flowing reference electrolyte, coatings can become detached from the reference element around which a free flow is possible, so that the reference electrode becomes unusable. In order to avoid these problems, with respect to the electrolytic channel, the reference element can be covered with an ion selective membrane, for example, that which is known from German Pat. No. 33 05 962. This can be a chloride-selective membrane, if the reference element comprises a silver chloride-coated silver wire and the reference electrolyte is a potassium chloride solution.

By covering the reference element with a correspondingly constructed ion selective membrane, the reference element does not come into contact with the reference electrolyte pumped through the electrolytic channel, but ions can pass from the reference electrolyte to the reference element through the membrane.

To permit simple replacement of the capillary body when the capillary channel is clogged, the capillary support can be screwed into a support member receiving the reference element and having the electrolytic channel, so that it can easily be detached therefrom and replaced by another capillary support. However, the capillary body is preferably detachably held in the capillary support and is therefore interchangeable, so that, after inserting a new capillary body, the capillary support can again be screwed into the support member.

BRIEF DESCRIPTION OF THE DRAWINGS

The invention is illustrated hereinafter relative to the drawings.

FIG. 2 is a sectional view of a reference electrode.

FIG. 3 is, partly as a side view and partly in section, the reference electrode of FIG. 2.

DESCRIPTION OF THE PREFERRED EMBODIMENT

Figure 1:
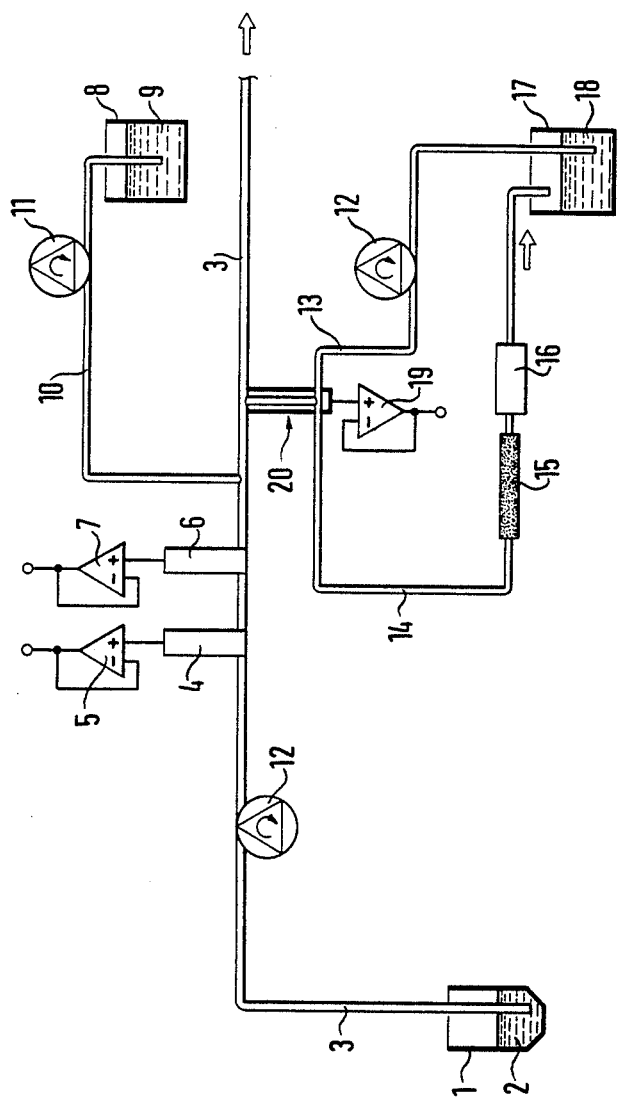
FIG. 1 is a schematic representation of the construction of an apparatus for measuring the ionic concentration in a sample liquid.

The apparatus shown in FIG. 1 contains a sample tank 1 with sample liquid 2 to be investigated. A line or measuring channel 3 passes from the sample tank. Two ion selective electrodes 4, 6, which are connected to amplifiers 5, 7, are inserted into channel 3 in one embodiment. Electrode 4 is, e.g., selective for potassium ions and electrode 6, e.g., for chlorine ions.

A reference electrode 20 with an amplifier 19 corresponding to amplifiers 5, 7 is also connected to measuring channel 3. The construction of the reference electrode will be described hereinafter relative to FIGS. 2 and 3.

A scavenging line 10, which is connected to a tank 8 for scavenging or cleansing fluid 9 is located on measuring channel 3 between electrode 6 and reference electrode 20. In order to pump scavenging or cleansing fluid from tank 8 into measuring channel 3, a hose pump 11 is provided, such as is, e.g., shown in U.S. Pat. No. 4,366,040. The scavenging fluid is used to remove from the measuring channel 3 the sample liquid of a preceding measurement prior to carrying out the present measurement.

To the end of the reference electrode 20 remote from measuring channel 3 is connected a line 13, 14, whose portion 13 extends into a tank 17 for reference electrolyte 18, e.g., a bimolar potassium chloride solution. In an extension of line 13, line 14 runs back from reference electrode 20 to tank 17 and in it is located a pressure reservoir 15 and a restrictor 16. The pressure reservoir 15 comprises a piece of elastically expandable hose, such as of silicone rubber. The restrictor 16 following the pressure reservoir 15 is a helically wound, inelastic hose, whose internal cross-section is at most half as large as the internal cross-section of the tubular pressure reservoir 15. Under the pressure of the entering reference electrolyte, the pressure reservoir 15 expands and the reference electrolyte is held for a certain time under pressure therein, because due to the limited internal cross-section of the inelastic hose of restrictor 16, it can only pass very slowly out of pressure reservoir 15 in the direction of tank 17.

In order to deliver the sample liquid 2 and the reference electrolyte 18, a single hose pump 12 is provided, which is in one embodiment constructed in the same way as the hose pump of U.S. Pat. No. 4,366,040, and on whose rotary piston are arranged in axially juxtaposed manner the hoses for the sample liquid and reference electrolyte. Thus, if the rotary piston of hose pump 12 is rotated, there is simultaneously a suction of sample liquid 2 from tank 1 into measuring channel 3 and a suction of reference electrolyte 18 from tank 17 into line 13, 14 and capillary channel 23. This pumping process is continued until, on the one hand, an adequate quantity of sample liquid 2 has been sucked into measuring channel 3, so that said sample liquid is in contact with the ion selective electrodes 4, 6 and the reference electrode 20, and on the other hand, by filling the pressure reservoir 15 such that a pressure is built up between the latter and the pump 12 in lines 13, 14. The gradual pressure drop due to reference electrolyte passing out of the pressure reservoir 15 via restrictor 16 is taken into account so that said pressure is maintained long enough to permit the desired measurement to be performed.

Reference electrode 20 is in one embodiment constructed in the way shown in FIGS. 2 and 3. Reference electrode 20 has a support body 25, in which is formed an electrolytic channel 28. For connecting electrolytic channel 28 to hose pump 12, the line 13, which is formed by a hose, is fixed by means of a screwed hose connection 27 and accompanied by the interposing of an O-ring in support body 25, while the connection to the pressure reservoir 15 is provided by a hose forming line 14, which is fixed in the support body 25 by means of a screwed hose connection 26 and while interposing an O-ring on the side opposite to hose 13. As shown, hoses 13, 14 are coaxial to one another and coaxial to electrolytic channel 28 in the vicinity of support body 25, the internal diameter thereof being substantially the same as the internal diameter of electrolytic channel 28.

A capillary support 21 is screwed into the support body 25 transversely at right angles to electrolytic channel 28. A capillary body 22, which is normally made from glass and has a through capillary channel 23, is inserted in capillary support 21. Capillary body 22 extends into the electrolytic channel 28, so that one end of capillary channel 23 is in contact with the reference electrolyte pumped through electrolytic channel 28. A gasket 24 is mounted on the free end of capillary support 21 and by means of said end of capillary support 21 can be connected to a corresponding connection in measuring channel 3, so as to bring the lower end of capillary channel 23 in FIG. 2 into contact with the sample liquid 2 pumped through measuring channel 3.

Perpendicularly with respect to electrolytic channel 28, but on the side opposite to capillary channel 23, a reference element 29 fixed in a contact rivet 30 is inserted in support body 25. Reference element 29 which, in one embodiment comprises a silver chloride-coated silver wire, is covered with a chloride-selective membrane 31, which on its lower side in FIGS. 2 and 3 is shaped in accordance with the wall of electrolytic channel 28 (FIG. 3), i.e., its cross-sectional shape does not change. In the case of a reference element of silver chloride-coated silver wire, and when using a potassium chloride solution as the reference electrolyte, membrane 31 for example comprises a PVC matrix with 82 percent PVC and 18 percent MTDDA-Cl, as is already used for chloride-selective electrodes (Mikrochimica Acta, Vienna, 1978 II, pp 235 to 246).

If pump 12 supplies reference electrolyte through hose 13 to reference electrode 20, it flows through electrolytic channel 28 and hose 14 and as a result of this flow and the construction of the electrolytic channel 28, there is no risk of air bubbles remaining in the opening of capillary channel 23 extending into electrolytic channel 28. As a result of the reference electrolyte flow through electrolytic channel 28, reference electrolyte passes into capillary channel 23 and is conveyed in measuring channel 3 until contact is made with the sample liquid 2, so that the reference electrolyte electrically connects membrane 31 to the sample liquid. In the case of a corresponding configuration of contact rivet 30, ionic conductivity exists from reference electrolyte 2 to reference element 29 via membrane 31 and consequently to the evaluation circuit and this constitutes a measure of the potential difference between the sample liquid and the reference electrolyte. If the capillary channel 23 becomes clogged in operation, it is merely necessary to detach reference electrode 20 from channel 3 after which the capillary support 21 can be unscrewed from support body 25 and capillary body 22 replaced by another capillary body.

We claim:

1. A process for measuring a potential difference between a flow of sample liquid delivered by pumping and a reference electrolyte, comprising the steps of:
    providing an apparatus defining a channel for a sample liquid flow and comprising a reference electrode in contact with said sample flow, said electrode comprising a reference element and defining a capillary channel having a first and second end and extending transversely to said sample flow, said first end opening into said sample flow and said second end receiving reference electrolyte to be fed into said capillary channel;
    pumping said sample flow transverse to said capillary channel through said sample flow channel; and
    pumping a flow of reference electrolyte transverse to said capillary channel and over said second end before said potential difference is measured.

2. The process according to claim 1, wherein said pumping of said sample liquid and said pumping of said reference electrolyte start and finish simultaneously.

3. The process according to claim 2, further comprising the step of passing said sample liquid flow and said reference electrolyte flow through respective hoses, each of which is in engagement with a rotary piston of a hose pump and is juxtaposed with the other in an axial direction of said piston.

4. A process for measuring an ionic concentration in a sample liquid comprising the process according to claim 1 and the further step of contacting said sample liquid flow with at least one ion selective electrode, and wherein said pumping of said flow of reference electrolyte comprises the steps of maintaining a pressure over said second end of said capillary channel by pumping said flow of reference electrolyte into a pressure reservoir from which said reference electrolyte can only slowly flow out.

* * * * *